(12) United States Patent
Ho

(10) Patent No.: US 6,328,782 B1
(45) Date of Patent: Dec. 11, 2001

(54) COMBINED SUPPORTED LIQUID MEMBRANE/STRIP DISPERSION PROCESS FOR THE REMOVAL AND RECOVERY OF RADIONUCLIDES AND METALS

(75) Inventor: W. S. Winston Ho, Lexington, KY (US)

(73) Assignee: Commodore Separation Technologies, Inc., New York, NY (US)

( * ) Notice: Subject to any disclaimer, the term of this patent is extended or adjusted under 35 U.S.C. 154(b) by 0 days.

(21) Appl. No.: 09/498,146

(22) Filed: Feb. 4, 2000

(51) Int. Cl.$^7$ .................................................. C22C 43/00
(52) U.S. Cl. ........................... 75/393; 210/682; 210/687; 210/688; 210/643; 210/651; 423/8
(58) Field of Search ..................................... 210/682, 687, 210/688, 643, 651; 423/8; 75/393

(56) References Cited

U.S. PATENT DOCUMENTS

| | | | |
|---|---|---|---|
| 5,114,579 | * 5/1992 | Takigawa | 210/638 |
| 5,507,949 | * 4/1996 | Ho | 210/490 |
| 5,666,642 | * 9/1997 | Hawthorne et al. | 423/2 |
| 5,868,935 | * 2/1999 | Sirkar et al. | 210/643 |
| 6,171,563 | * 1/2001 | Ho | 423/54 |

OTHER PUBLICATIONS

Chiarizia, "Application of Supported Liquid Membranes for Removal of Nitrate, Technetium (VII) and Chromium (VI) from Groundwater," *J. Membrane Sci.*, 55, 39–64 (1991).

Dozol et al., "A Solution for Cesium Removal from High-–Salinity Acidic or Alkaline Liquid Waste: the Crown Calix [4]arenes," *Sep. Sci. Technol.*, 34, 877–909 (1999).

Dozol et al., "Stability of Flat Sheet Supported Liquid Membranes in the Transport of Radionuclides from Reprocessing Concentrate Solutions," *J. Membrane Sci.*, 82, 237–246 (1993).

Dreher et al., "Instability Mechanisms of Supported Liquid Membranes," *Sep. Sci. Technol.*, 33, 835–853 (1998).

Eroglu et al., "Extraction of Strontium Ions with Emulsion Liquid Membrane Technique," *J. Membrane Sci.*, 80, 319–325 (1993).

Ho et al., eds., *Membrane Handbook*, Chapman & Hall, New York, 1992).

Jönsson, N. Ä., "Chemical structure and teratogenic properties," *Acta Pharmaceutica Suecica*, 9, 522–542 (1972).

Kedari et al., "Selective Permeation of Plutonium (IV) Through Supported Liquid Membrane Containing 2–Ethylhexyl 2–Ethylhexyl Phosphonic Acid as Ion Carrier," *J. Membrane Sci.*, 156, 187–196 (1999).

Kemperman et al., "Stability of Supported Liquid Membranes: State of the Art," *Sep. Sci. Technol.*, 31, 2733 (1996).

Nechaev et al., "Supported Liquid Membranes in Radioactive Waste Treatment Processes: Recent Experience and Prospective," in S. Slate, R. Baker, and G. Benda, eds., *Proceedings of Fifth International Conference on Radioactive Waste Management and Environmental Remediation*, vol. 2, American Society of Mechanical Engineers, New York, 1995.

Raghuraman et al., "Extraction with Emulsion Liquid Membranes in a Hollow–Fiber Contactor," *AIChE J.*, 39, 1885–1889 (1993).

Viñs et al., "C–substituted bis(dicarbollide) Metal Compounds as Sensors and Extractants of Radionuclides from Nuclear Wastes," *J. Org. Chem.*, 581, 188–193 (1999).

* cited by examiner

Primary Examiner—Ngoclan Mai
(74) Attorney, Agent, or Firm—Kilpatrick Stockton LLP

(57) ABSTRACT

The present invention provides a novel process for the removal and recovery of radionuclides from waste waters and process streams. The process of the present invention utilizes a combination of a supported liquid membrane (SLM) and a strip dispersion to improve extraction of the target species while increasing membrane stability and reducing processing costs. Additionally, the invention provides a family of new extractants, alkyl phenylphosphonic acids, for the removal and recovery of radionuclides and/or metals, including the use of the new extractants in the process. The new extractant selectively removes radionuclides and metals from the feed stream to provide a concentrated strip solution of the target species.

35 Claims, 2 Drawing Sheets

US 6,328,782 B1

COMBINED SUPPORTED LIQUID MEMBRANE/STRIP DISPERSION PROCESS FOR THE REMOVAL AND RECOVERY OF RADIONUCLIDES AND METALS

FIELD OF THE INVENTION

The present invention relates to the removal and recovery of radionuclides and metals from feed solutions, such as waste waters and process streams, using supported liquid membrane technology.

BACKGROUND OF THE INVENTION

Liquid membranes combine extraction and stripping, which are normally carried out in two separate steps in conventional processes such as solvent extractions, into one step. A one-step liquid membrane process provides the maximum driving force for the separation of a targeted species, leading to the best clean-up and recovery of the species (W. S. Winston Ho and Kamalesh K. Sirkar, eds., *Membrane Handbook,* Chapman & Hall, New York, 1992).

There are two types of liquid membranes: (1) supported liquid membranes (SLMs) and (2) emulsion liquid membranes (ELMs). In SLMs, the liquid membrane phase is the organic liquid imbedded in pores of a microporous support, e.g., microporous polypropylene hollow fibers (W. S. Winston Ho and Kamalesh K. Sirkar, eds., *Membrane Handbook,* Chapman & Hall, New York, 1992). When the organic liquid contacts the microporous support, it readily wets the pores of the support, and the SLM is formed.

For the extraction of a target species from a feed solution, the organic-based SLM is placed between two aqueous solutions—the feed solution and the strip solution where the SLM acts as a semi-permeable membrane for the transport of the target species from the feed solution to the strip solution. The organic liquid in the SLM is immiscible in the aqueous feed and strip streams and contains an extractant, a diluent which is generally an inert organic solvent, and sometimes a modifier.

The use of SLMs to remove radionuclides from aqueous feed solutions has been long pursued in the scientific and industrial community. Nechaev et al. (A. F. Nechaev, V. V. Projaev, V. P. Kapranchik, "Supported Liquid Membranes in Radioactive Waste Treatment Processes: Recent Experience and Prospective", in S. Slate, R. Baker, and G. Benda, eds., *Proceedings of Fifth International Conference on Radioactive Waste Management and Environmental Remediation,* Volume 2, American Society of Mechanical Engineers, New York, 1995) have reported on the experience and prospective of using SLMs in radioactive waste treatment processes, and the transport of uranyl ion across SLMs has been studied extensively (J. P. Shukla and S. K. Misra, "Uranyl Ion Transport Across Tri-n-butyl Phosphate/n-Dodecane Liquid Membranes", *Proceedings of the International Symposium on Uranium Technology,* Bhabha Atomic Research Centre, Bombay, India, pp. 939–946, 1991; M. A. Chaudhary, "Separation of Some Metal Ions Using Coupled Transport Supported Liquid Membranes", in H. Javed, H. Pervez, and R. Qadeer, *Modern Trends in Contemporary Chemistry,* Scientific Information Division PINSTECH, Islamabad, Pakistan, pp. 123–131, 1993).

Chiarizia et al. (R. Chiarizia, E. P. Horwitz, and K. M. Hodgson, *An Application of Supported Liquid Membranes for Removal of Inorganic Contaminants from Groundwater,* DOE Report No. DE92006971, 1991) have reviewed and summarized the results of an investigation on the use of SLMs for the removal of uranium and some inorganic contaminants, including technetium, from the Hanford site groundwater. Chiarizia (R. Chiarizia, "Application of Supported liquid Membranes for Removal of Nitrate, Technetium (VII) and Chromium (VI) from Groundwater", *J. Membrane Sci.,* 55, 39–64 (1991)) has described the separation of technetium (VII) and uranium (VI) from synthetic Hanford site groundwater using SLMs. Dozol et al. (J. F. Dozol, J. Casas, and A. Sastre, "Stability of Flat Sheet Supported Liquid Membranes in the Transport of Radionuclides from Reprocessing Concentrate Solutions", *J. Membrane Sci.,* 82, 237–246 (1993)) have studied the stability of flat sheet SLMs in the transport of radionuclides.

Recently, Dozol et al. (J. F. Dozol, N. Simon, V. Lamaare, H. Rouquette, S. Eymard, B. Tournois, D. De Marc, and R. M. Macias, "A Solution for Cesium Removal from High-Salinity Acidic or Alkaline Liquid Waste: the Crown Calix [4]arenes", *Sep. Sci. Technol.,* 34, 877–909 (1999)) have described the use of the extractant, Calix[4]arenes monocrown or biscrown, blocked in 1,3 alternative cone conformation, in SLMs for the removal of cesium from high-salinity acidic or alkaline liquid waste. Kedari et al. (C. S. Kedari, S. S. Pandit, and A. Ramanujam, "Selective Permeation of Plutonium (IV) through Supported Liquid Membrane Containing 2-Ethylhexyl 2-Ethylhexyl Phosphonic Acid as Ion Carrier", *J. Membrane Sci.,* 156, 187–196 (1999)) have studied the selective permeation of plutonium (IV) through a SLM containing 2-ethylhexyl 2-ethylhexyl phosphonic acid as the ion carrier.

One disadvantage of SLMs is their instability due mainly to loss of the membrane liquid (organic solvent, extractant, and/or modifier) into the aqueous phases on each side of the membrane (A. J. B. Kemperman, D. Bargeman, Th. Van Den Boomgaard, H. Strathmann, "Stability of Supported Liquid Membranes: State of the Art", *Sep. Sci. Technol.,* 31, 2733 (1996); T. M. Dreher and G. W Stevens, "Instability Mechanisms of Supported Liquid Membranes", *Sep. Sci. Technol.,* 33, 835–853 (1998); J. F. Dozol, J. Casas, and A. Sastre, "Stability of Flat Sheet Supported Liquid Membranes in the Transport of Radionuclides from Reprocessing Concentrate Solutions", *J. Membrane Sci.,* 82, 237–246 (1993)). The prior art has attempted to solve this problem through the combined use of SLM with a module containing two set of hollow fibers, i.e., the hollow-fiber contained liquid membrane (W. S. Winston Ho and Kamalesh K. Sirkar, eds., *Membrane Handbook,* Chapman & Hall, New York, 1992). In this configuration with two sets of microporous hollow-fiber membranes, one carries the aqueous feed solution, and the other carries the aqueous strip solution. The organic phase is contained between the two sets of hollow fibers by maintaining the aqueous phases at a higher pressure than the organic phase. The use of the hollow-fiber contained liquid membrane increases membrane stability, because the liquid membrane may be continuously replenished. However, this configuration is not advantageous because it requires mixing two sets of fibers to achieve a low contained liquid membrane thickness.

In ELMs, an emulsion acts as a liquid membrane for the separation of the target species from a feed solution. An ELM is created by forming a stable emulsion, such as a water-in-oil emulsion, between two immiscible phases, followed by dispersion of the emulsion into a third, continuous phase by agitation for extraction. The membrane phase is the oil phase that separates the encapsulated, internal aqueous droplets in the emulsion from the external, continuous phase (W. S. Winston Ho and Kamalesh K. Sirkar, eds., *Membrane Handbook,* Chapman & Hall, New York, 1992). The species-extracting agent is contained in the membrane phase, and the stripping agent is contained in the internal aqueous droplets. Emulsions formed from these two phases are generally stabilized by use of a surfactant. The external, continuous phase is the feed solution containing the target species. The target species is extracted from the aqueous feed solution into the membrane phase and then stripped into the aqueous droplets in the emulsion. The target species can then be recovered from the internal aqueous phase by breaking the emulsion, typically via electrostatic coalescence, followed by electroplating or precipitation.

The use of ELMs to remove radionuclides from aqueous feed solutions has also been long pursued in the scientific and industrial community. The ELMs for the removal of radionuclides, including strontium, cesium, technetium, and uranium, have been described in detail (W. S. Winston Ho and Kamalesh K. Sirkar, eds., *Membrane Handbook,* Chapman & Hall, New York, 1992). The extraction of strontium with the ELM technique has been investigated (I. Eroglu, R. Kalpakci, and G. Gunduz, "Extraction of Strontium Ions with Emulsion Liquid Membrane Technique", *J. Membrane Sci.*, 80, 319–325 (1993)).

One disadvantage of ELMs is that the emulsion swells upon prolonged contact with the feed stream. This swelling causes a reduction in the stripping reagent concentration in the aqueous droplets which reduces stripping efficiency. It also results in dilution of the target species that has been concentrated in the aqueous droplets, resulting in lower separation efficiency of the membrane. The swelling further results in a reduction in membrane stability by making the membrane thinner. Finally, swelling of the emulsion increases the viscosity of the spent emulsion, making it more difficult to demulsify. A second disadvantage of ELMs is membrane rupture, resulting in leakage of the contents of the aqueous droplets into the feed stream and a concomitant reduction of separation efficiency. Raghuraman and Wiencek (B. Raghuraman and J. Wiencek, "Extraction with Emulsion Liquid Membranes in a Hollow-Fiber Contactor", *AIChE J.*, 39, 1885–1889 (1993)) have described the use of microporous hollow-fiber contactors as an alternative contacting method to direct dispersion of ELMs to minimize the membrane swelling and leakage. This is due to the fact that the hollow-fiber contactors do not have the high shear rates typically encountered with the agitators used in the direct dispersion. Additional disadvantages include the necessary process steps for making and breaking the emulsion.

Thus, there is a need in the art for an extraction process which maximizes the stability of the SLM membrane, resulting in efficient removal and recovery of radionuclides from the aqueous feed solutions.

There is also a need in the art for extractants which selectively remove a given target species from the feed stream.

SUMMARY OF THE INVENTION

The present invention relates generally to a process for the removal and recovery of target species from a feed solution using a combined SLM/strip dispersion. The invention also relates to a new family of extractants that are useful for the removal and recovery of radionuclides and metals.

In one embodiment, the present invention relates to a process for the removal and recovery of one or more radionuclides from a feed solution which comprises the following steps. First, a feed solution containing one or more radionuclides is passed on one side of the SLM embedded in a microporous support material and treated to remove the radionuclides by the use of a strip dispersion on the other side of the SLM. The strip dispersion can be formed by dispersing an aqueous strip solution in an organic liquid, for example, using a mixer. Second, the strip dispersion, or a part of the strip dispersion, is allowed to stand, resulting in separation of the dispersion into two phases: the organic liquid phase and the aqueous strip solution phase containing a concentrated radionuclide solution.

The continuous organic phase of the strip dispersion readily wets the pores of a microporous support to form a stable SLM. The process of the present invention provides a number of operational and economic advantages over the use of conventional SLMs.

In another embodiment, the present invention relates to a process for the removal and recovery of one or more metals from a feed solution which comprises the following steps. First, a feed solution containing one or more metals is passed on one side of the SLM embedded in a microporous support material and treated to remove the metals by the use of a strip dispersion on the other side of the SLM. As described above, the strip dispersion can be formed by dispersing an aqueous strip solution in an organic liquid, for example, using a mixer. The strip dispersion, or a part of the strip dispersion, is then allowed to stand, resulting in separation of the dispersion into two phases: the organic liquid phase and the aqueous strip solution phase containing a concentrated metal solution.

In yet another embodiment, the present invention relates to a family of new extractants, alkyl phenylphosphonic acids, e.g., 2-butyl-1-octyl phenylphosphonic acid (BOPPA) and 2-octyl-1-dodecyl phenylphosphonic acid (C20 ODPPA), which are useful in both conventional SLMs and the process of the present invention for the removal and recovery of radionuclide and/or metal species, also called herein the "target species." Use of the new extractants result in improved extraction and an increased concentration of the target species in the aqueous strip solution.

Thus, it is an object of the present invention to provide an SLM process for the removal and recovery of target species which provides increased membrane stability.

It is another object of the invention to provide an SLM process having high flux.

It is yet another object of the present invention to provide an SLM process having improved recovery of the target species to provide a concentrated strip solution.

It is a further object of the invention to provide an SLM process for the removal and recovery of a target species from a feed solution which exhibits decreased operation costs and a decreased capital investment over convention SLM processes.

It is an object of the present invention to provide an SLM process for the removal and recovery of radionuclides from a to feed solution.

It is another object of the present invention to provide a process for the removal and recovery of metals from a feed solution.

It is yet another object of the present invention to provide a process for the removal and recovery of strontium, cesium, technetium, uranium, boron, plutonium, cobalt, or americium from a feed solution.

It is a further object of the invention to provide a process for the removal and recovery of calcium, magnesium, and/or zinc from a feed solution.

It is an object of the invention to provide a family of new extractants, alkyl phenylphosphonic acids, for the removal of target species.

It is also an object of the invention to provide the compound 2-butyl-1-octyl phenylphosphonic acid (BOPPA) for the removal of target species.

It is another object of the invention to provide the compound 2-octyl-1-dodecyl phenylphosphonic acid (C20 ODPPA) for the removal of target species.

It is yet another object of the invention to provide a process for the removal of strontium, cesium, technetium, uranium, boron, plutonium, cobalt, or americium using an alkyl phenylphosphonic acid.

It is another object of the invention to provide a process for the removal of strontium, cesium, technetium, uranium, boron, plutonium, cobalt, or americium using 2-butyl-1-octyl phenylphosphonic acid (BOPPA).

It is another object of the invention to provide a process for the removal of strontium, cesium, technetium, uranium, boron, plutonium, cobalt, or americium using 2-octyl-1-dodecyl phenylphosphonic acid (C20 ODPPA).

It is another object of the invention to provide a process for the removal of calcium, magnesium, and/or zinc using an alkyl phenylphosphonic acid.

It is another object of the invention to provide a process for the removal of calcium, magnesium, and/or zinc using 2-butyl-1-octyl phenylphosphonic acid (BOPPA).

It is another object of the invention to provide a process for the removal of calcium, magnesium, and/or zinc using 2-octyl-1-dodecyl phenylphosphonic acid (C20 ODPPA).

DESCRIPTION OF THE PREFERRED EMBODIMENTS

The present invention relates to a process for the removal and recovery of a target species. These target species include, but are not limited to, radionuclides, such as strontium, cesium, technetium, uranium, boron, plutonium, cobalt, and americium, and metals, such as calcium, magnesium, and zinc, from a feed solution, such as waste waters or process streams. This new process employs a combination of a supported liquid membrane (SLM) and a strip dispersion.

The present invention also relates to a family of new extractants, alkyl phenylphosphonic acids. Examples of preferred alkyl phosphonic acids include, but are not limited to, 2-butyl-1-octyl phenylphosphonic acid (BOPPA) and 2-octyl-1-dodecyl phenylphosphonic acid (C20 ODPPA). These extractants are useful in both conventional SLMs and the present process for the removal and recovery of radionuclides, such as strontium, cesium, plutonium, cobalt, and americium, and metals, such as calcium, magnesium, and zinc. Use of the new extractants results in improved extraction of the target species from the feed solution and an increased concentration of the target species in the aqueous strip solution.

In one embodiment, the present invention relates to a process for the removal and recovery of one or more radionuclides from a feed solution which comprises the following steps. First, a feed solution containing one or more radionuclides is passed on one side of the SLM embedded in a microporous support material and treated to remove the radionuclides by the use of a strip dispersion on the other side of the SLM. The strip dispersion can be formed by dispersing an aqueous strip solution in an organic liquid, for example, using a mixer. Second, the strip dispersion, or a part of the strip dispersion, is allowed to stand, resulting in separation of the dispersion into two phases: the organic liquid phase and the aqueous strip solution phase containing a concentrated radionuclide solution.

In another embodiment, the present invention relates to a process for the removal and recovery of one or more metals from a feed solution which comprises the following steps. First, a feed solution containing one or more metals is passed on one side of the SLM embedded in a microporous support material and treated to remove the metals by the use of a strip dispersion on the other side of the SLM. As described above, the strip dispersion can be formed by dispersing an aqueous strip solution in an organic liquid, for example, using a mixer. The strip dispersion, or a part of the strip dispersion, is then allowed to stand, resulting in separation of the dispersion into two phases: the organic liquid phase and the aqueous strip solution phase containing a concentrated metal solution.

Figure 1:
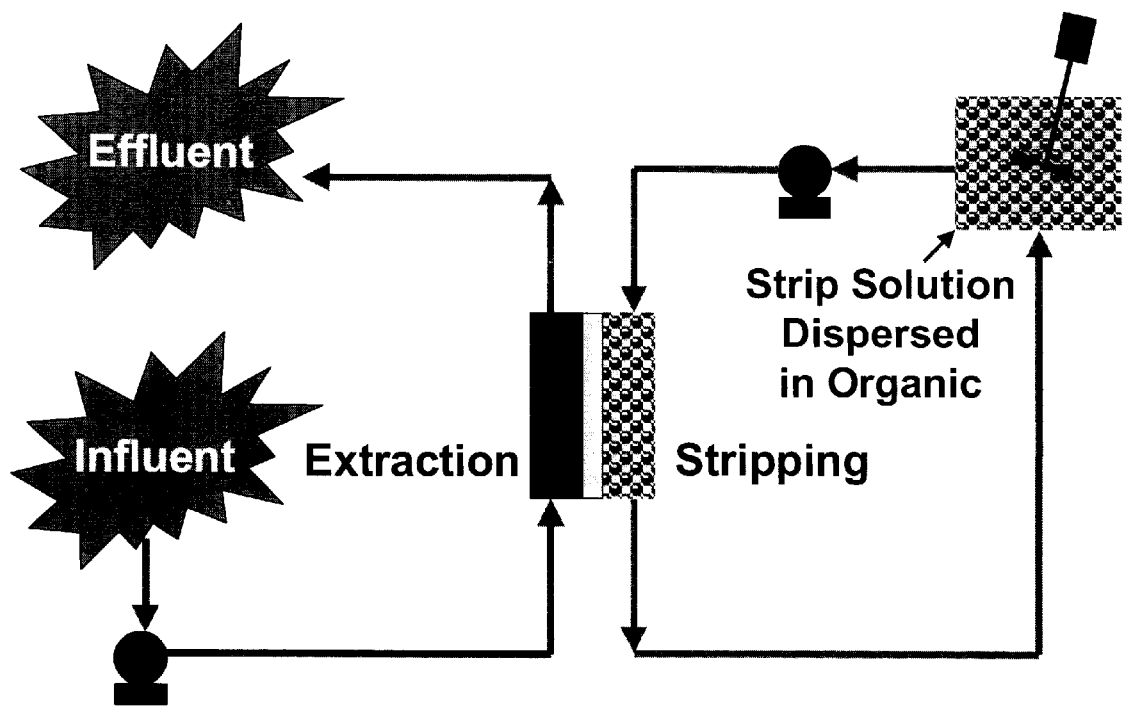
FIG. 1 is a schematic representation of the combined supported liquid membrane/strip dispersion of the present invention.

While any SLM configuration may be employed in the process of the invention, the preferred configuration employs a hollow fiber module as the liquid membrane microporous support. Such hollow fiber modules consist of microporous hollow fibers arranged in a shell-and-tube configuration. In the present invention, the strip dispersion is passed through either the shell side of the module or the tube side of the module, and the aqueous feed solution containing the target species for extraction is passed through the opposing side of the module. The use of the hollow fiber system in the combined SLM/strip dispersion process allows continuous replenishment of the strip dispersion as shown in FIG. 1, ensuring a stable and continuous operation.

For the purposes of the invention, strip dispersion is defined as a mixture of an aqueous phase and an organic phase. The aqueous phase of the dispersion comprises an aqueous strip solution, while the organic phase comprises an extractant or extractants in an organic liquid. The dispersion is formed by the mixing of the aqueous and organic phases as shown in FIG. 1. This combination results in droplets of the aqueous strip solution in a continuous organic phase. The dispersion is maintained during the extraction process due to the flow of the dispersion through a membrane module, e.g., a hollow-fiber module. The continuous organic phase of the strip dispersion readily wets the hydrophobic pores of the microporous hollow fibers in the module, forming a stable liquid membrane.

Figure 2:
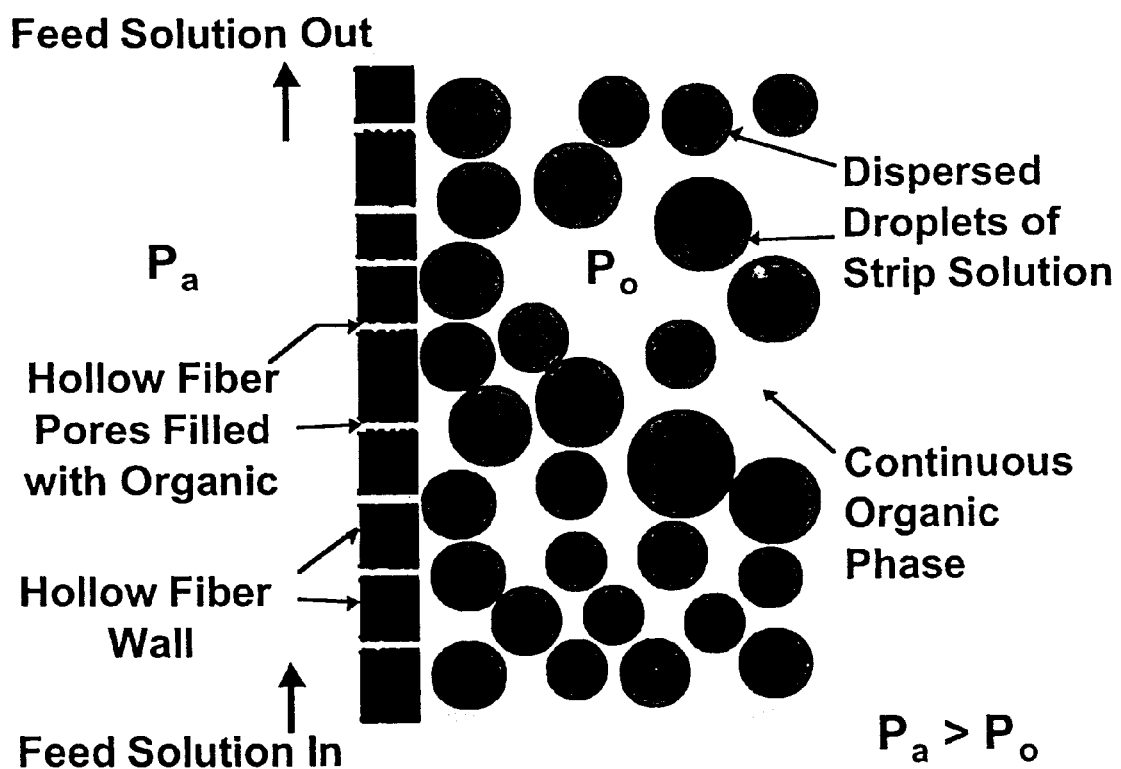
FIG. 2 is an enlarged view of the schematic representation of the combined supported liquid membrane/strip dispersion of the present invention.

FIG. 2 shows an enlarged view of a schematic representation of the SLM with strip dispersion of the present invention. A low pressure, $P_a$, which is typically less than approximately 2 psi, is applied on the feed solution side of the SLM. The pressure $P_a$ is greater than the pressure, $P_o$, on the strip dispersion side of the SLM. This difference in pressure prevents the organic solution of the strip dispersion from passing through the pores to come into the feed solution side. The dispersed droplets of the aqueous strip solution in a typical size of about 80 to about 800 micrometers and are orders of magnitude larger than the pore size of the microporous support employed for the SLM, which is in the order of approximately 0.03 micrometer. Thus, these droplets are retained on the strip dispersion side of the SLM and cannot pass through the pores to go to the feed solution side.

In this SLM/strip dispersion system, there is a constant supply of the organic membrane solution, i.e. the organic phase of the strip dispersion, into the pores. This constant supply of the organic phase ensures a stable and continuous operation of the SLM. In addition, the direct contact between the organic and strip phases provides efficient mass transfer for stripping. The organic and strip phases can be mixed, for example, with high-shear mixing, to increase the contact between the two phases.

Once removal of the target species is complete, the mixer for the strip dispersion is stopped, and the dispersion is allowed to stand until it separates into two phases, the organic membrane solution and the concentrated strip solution. The concentrated strip solution is the product of this process.

The feed solution includes, but is not limited to, waste waters or process streams containing radionuclides or metals. The to radionuclides include, but are not limited to, strontium, cesium, technetium, uranium, boron, plutonium, cobalt, and americium. The metals include, but are not limited to, calcium, magnesium, and zinc.

The microporous support employed in the invention is comprised of, for example, microporous polypropylene, polytetrafluoroethylene, polyethylene, polysulfone, polyethersulfone, polyetheretherketone, polyimide, polyamide, or mixtures thereof. The preferred microporous support is microporous polypropylene hollow fibers.

The aqueous portion of the strip dispersion comprises an aqueous acid solution, such as a mineral acid. Examples of mineral acids useful in the present invention include, but are not limited to, sulfuric acid ($H_2SO_4$), hydrochloric acid (HCl), nitric acid ($HNO_3$), and acetic acid ($CH_3COOH$). The acid is present in a concentration between about 0.1 M and about 18 M. The preferred concentration for the acid solution is between about 1 M and about 3 M.

The continuous organic liquid phase into which the aqueous strip solution is dispersed contains an extractant or extractants. The extractant is capable of extracting the target species contained in the feed solution. Typical extractants which are known in the art for extraction of species from waste waters or process streams may be employed in the present strip dispersion. Selection of such extractants based upon the specific target species to be extracted is within the level of skill in the art.

The organic liquid of the present strip dispersion optionally comprises a hydrocarbon solvent or mixture. The hydrocarbon solvent or mixture has a number of carbon atoms per solvent molecule ranging from 6 to 18, preferably from 10 to 14. The hydrocarbon solvent includes, for example, n-decane, n-undecane, n-dodecane, n-tridecane, n-tetradecane, isodecane, isoundecane, isododecane, isotridecane, isotetradecane, isoparaffinic hydrocarbon solvent (with a flash point of 92° C., a boiling point of 254° C., a viscosity of 3 cp (at 25° C.), and a density of 0.791 g/ml (at 15.6° C.)) or mixtures thereof.

The organic liquid of the present strip dispersion optionally contains a modifier to enhance the complexation and/or stripping of the target species. The modifier can be, for example, an alcohol, a nitrophenyl alkyl ether, a trialkyl phosphate or mixtures thereof. The alcohol can be, for example, hexanol, heptanol, octanol, nonanol, decanol, undecanol, dodecanol, tridecanol, tetradecanol, pentadecanol, hexadecanol, heptadecanol, octadecanol or mixtures thereof. The nitrophenyl ether can be, for example, o-nitrophenyl octyl ether (o-NPOE), o-nitrophenyl heptyl ether, o-nitrophenyl hexyl ether, o-nitrophenyl pentyl ether (o-NPPE), o-nitrophenyl butyl ether, o-nitrophenyl propyl ether or a mixture thereof. The trialkyl phosphate can be, for example, tributyl phosphate, tris(2-ethylhexyl)phosphate or mixtures thereof.

The organic liquid of the present strip dispersion comprises about 2% to about 100% (approximately 0.05M–3M) extractant and about 0% to about 20% modifier in a hydrocarbon solvent or mixture. More preferably, the organic liquid of the present strip dispersion comprises about 5% to about 40% extractant and about 1% to about 10% modifier in a hydrocarbon solvent or mixture. Even more preferably, the organic liquid comprises 5% to about 40% extractant and about 1% to about 10% dodecanol in an isoparaffinic hydrocarbon solvent or in n-dodecane. All percentages are by weight unless specified otherwise.

The present invention has several advantages over conventional SLM technology. These advantages include increased membrane stability, reduced costs, increased simplicity of operation, improved flux, and improved recovery of target species concentration.

The present invention provides a constant supply of the organic membrane solution into the pores of the hollow fiber support. This constant supply results in an SLM which is more stable than conventional SLMs, ensuring stable and continuous operation. This constant supply also eliminates the need for recharging membrane modules, which is required with conventional SLMs. Further, it eliminates the need for a second set of membrane modules for use during recharging of the first set of membrane modules. Thus, the present invention decreases not only operational costs but also the initial capital investment in the system. The present invention also increases simplicity of the removal operation.

The present invention provides direct contact between the organic/extraction phase and aqueous strip phase. Mixing of these phases provides an extra mass transfer surface area in addition to the area given by the hollow fibers, leading to extremely efficient stripping of the target species from the organic phase. This efficient stripping enhances the flux for the extraction of many targeted species, resulting in unexpectedly high flux results as compared with conventional SLM extractions.

The present invention comprises a new type of SLM which provides increased flexibility of aqueous strip/organic volume ratio. This flexibility allows the use of a smaller volume of aqueous strip solution to obtain a higher concentration of the recovered species in the aqueous strip solution. The concentrated strip solution is a valuable product for resale or reuse.

The present invention also encompasses a family of new extractants, alkyl phenylphosphonic acids, which have advantageous properties over prior art extractants. The alkyl group of the alkyl phenylphosphonic acid is paraffinic (saturated) and includes from 6 to 26 carbon atoms. The new alkyl phenylphosphonic acids include 2-butyl-1-octyl phenylphosphonic acid (BOPPA; C12 alkyl group), 2-hexyl-1-decyl phenylphosphonic acid (C16 alkyl group), 2-octyl-1-decyl/2-hexyl-1-dodecyl phenylphosphonic acid (C18 alkyl group), 2-octyl-1-dodecyl phenylphosphonic acid (C20 ODPPA; C20 alkyl group), hexyl phenylphosphonic acid (C6 alkyl group), heptyl phenylphosphonic acid (C7 alkyl group), octyl phenylphosphonic acid (C8 alkyl group), nonyl phenylphosphonic acid (C9 alkyl group), decyl phenylphosphonic acid (C10 alkyl group), undecyl phenylphosphonic acid (C11 alkyl group), dodecyl phenylphosphonic acid (C12 alkyl group), tridecyl phenylphosphonic acid (C13 alkyl group), tetradecyl phenylphosphonic acid (C14 alkyl group), pentadecyl phenylphosphonic acid (C15 alkyl group), hexadecyl phenylphosphonic acid (C16 alkyl group), heptadecyl phenylphosphonic acid (C17 alkyl group), octadecyl phenylphosphonic acid (C18 alkyl group), nonadecyl phenylphosphonic acid (C19 alkyl group), decadecyl phenylphosphonic acid (C20 alkyl group), undecadecyl phenylphosphonic acid (C21 alkyl group), dodecadecyl phenylphosphonic acid (C23 alkyl group), tridecadecyl phenylphosphonic acid (C23 alkyl group), tetrdecadecyl phenylphosphonic acid (C24 alkyl group), pentadadecyl phenylphosphonic acid (C25 alkyl group), hexadecadecyl phenylphosphonic acid (C26 alkyl group), and mixtures thereof. Preferred alkyl phenylphosphonic acids include BOPPA and (C20 ODPPA).

The new extractants are useful for the removal and recovery of radionuclides, such as strontium, cesium, plutonium, cobalt, and americium, and metal species, such as calcium, magnesium, and zinc. In a preferred embodiment, the alkyl phenylphosphonic acid is employed as the extractant in the strip dispersion in the process of the invention. As seen from the examples appended below, the alkyl phenylphosphonic acid has significantly increases the extraction of strontium from feed solutions. The new extractant also extends the SLM operation to a lower pH range to better utilize the available surface area of the hollow-fiber module. For example, for the removal of strontium, the pH has been reduced from 4.5 to 3.

The alkyl phenylphosphonic acid may be synthesized, for example, by reacting an alcohol containing from 6 to 26 carbon atoms and phenylphosphonyl dichloride in an organic solvent, such as pyridine. Preferred temperatures for the reaction are between about 0 and 10° C. The reaction is quenched by adding concentrated HCl and ice to the reaction mixture, resulting in a solution having a pH of 1. The alkyl phenylphosphonic acid can then be extracted from the reaction mixture using a solvent, such as toluene. The alkyl phenylphosphonic acid/solvent solution was washed with 1 M HCl solution and dried, for example, with $MgSO_4$ to produce a clear solution. The alkyl phenylphosphonic acid can then be recovered by evaporating the solvent from the solution in any manner.

BOPPA may be synthesized, for example, by reacting 2-butyl-1-octanol and phenylphosphonyl dichloride in an organic solvent. Preferred temperatures for the reaction are between about 0 and 10° C. The reaction is quenched by adding concentrated HCl and ice to the reaction mixture, resulting in a solution having a pH of 1. The BOPPA can then be extracted from the reaction mixture using a solvent, such as toluene. The BOPPA/solvent solution was washed with 1 M HCl solution and dried, for example, with $MgSO_4$ to produce a clear solution. The BOPPA can then be recovered by evaporating the solvent from the solution in any manner. The other alkyl phenylphosphonic acids, including 2-hexyl-1-decyl (C16) phenylphosphonic acid, 2-octyl-1-decyl/2-hexyl-1-dodecyl (C18) phenylphosphonic acid, 2-octyl-1-dodecyl (C20) phenylphosphonic acid, can be synthesized in a similar manner.

This invention is further illustrated by the following examples, which are not to be construed in any way as imposing limitations upon the scope thereof. To the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

General Procedure

The strip dispersion for each of the following examples was prepared by mixing an aqueous strip solution in a quantity of, for example, 200 ml, and an organic extractant solution (for example, dodecane containing 2 wt. % dodecanol and 8 wt. % extractant) in a quantity of, for example, 600 ml, in a Fisher brand mixer with a 2-inch diameter, 6-bladed, high-shear impeller at 500 rpm as measured by an Ono Sokki HT-4100 tachometer. The mixer was plugged into a varistat to allow for adjustable speed control. The impeller was initially started at 50% of its full power and the varistat at 80%.

All of the following examples were run in countercurrent fashion with the feed solution passed through the tube side of the microporous polypropylene hollow fiber module. The hollow-fiber moldule was 2.5 inches in diameter and 8 inches in length, providing a surface area of 1.4 m². The process was first started by passing water through the hollow fiber module. The pressures were adjusted to provide a positive pressure on the feed side of the hollow fiber module. Once the pressures were adjusted and stable, the water was replaced with the feed solution. A positive pressure was maintained on the feed side to prevent the organic phase in the shell side from passing through the pores of the hollow fibers.

The pressure of the inlet on the shell side was maintained at 1.25 psi and the outlet pressure of the feed side was set at 3.25 psi, thus maintaining a 2 psi differential between the two sides. In each of the runs, the feed flow was adjusted to give a flow rate of approximately 0.84 liter/min at these pressures. The typical feed solution volume for these experiments was 4 liters.

Samples from the feed solution and the strip dispersion were taken at timed intervals. The strip dispersion samples were allowed to stand until phase separation occurred. The aqueous phase from the strip dispersion sample was then collected and centrifuged to facilitate complete separation. The aqueous phase samples from the strip dispersion samples and the feed solution samples were then analyzed by inductively coupled plasma (ICP) spectrometry.

The flux of a species removed from the feed solution can be defined by the following formula:

$$flux = \frac{V \Delta C}{tA}$$

where V is the volume of the feed solution treated; $\Delta C$ is the concentration change in the feed solution; t is the time at which the sample was taken; and A is the membrane surface area. The flux of the species was calculated from the above equation.

The mass transfer coefficient k of the species removed from the feed solution can be defined by the following formula:

$$k = \frac{V}{tA} \ln\left(\frac{C_o}{C_t}\right)$$

where $C_o$ is the initial concentration of the species in the feed solution; $C_t$ is the concentration of the species in the feed solution at time t; t is the time; and the rest of the symbols are as defined above. The mass transfer coefficient k of the species was calculated from the above equation.

Example 1

A fresh solution of 3 M $H_2SO_4$ was prepared for use as the strip solution. A strip dispersion was then prepared by mixing together 250 ml of the 3 M $H_2SO_4$ solution and 750 ml of n-dodecane containing 2% dodecanol and 8% 2-butyl-1-octyl phenylphosphonic acid (BOPPA) as described in the general procedure above. The strip dispersion was fed into the shell side of a polypropylene hollow fiber module. A feed solution containing the following metals was passed into the tube side of the hollow fiber module: strontium (Sr; 5 ppm), calcium (Ca; 80 ppm), magnesium (Mg; 20 ppm), or zinc (Zn; 50 ppm). The pH of the feed solution was maintained at 3.0+/−0.1 by adding 5 M NaOH as needed. Samples of the feed and strip solutions were collected at timed intervals as described in the general procedure above and analyzed by ICP. Fluxes and k values were then calculated and are reported in Tables 1 to 4.

The organic phase extracted the Sr and other ions well at pH 3, but the stripping was poor (1–3 ppm). The Mg and Sr were extracted to a similar degree, while Ca was removed after a 15 minute run. Therefore, 1 M HCl was used as the strip solution for Example 2.

TABLE 1

| Sr Results | | BOPPA | | pH ~3.0 ± 0.1 | | Dispersion Strip | 3M $H_2SO_4$ |
|---|---|---|---|---|---|---|---|
| Time (mins.) | pH | Strip (ppm) | Strip Flux g/(m²*hr) | Feed (ppm) | Ave. Flux g/(m²*hr) | Feed Flux g/(m²*hr) | k value cm/sec |
| 0 | 3.0 | 0 | | 5.45 | | | |
| 5 | | | | 5.03 | 0.00720 | 0.00720 | 0.0000382 |
| 10 | | 1.53 | 0.001284 | 3.08 | 0.02031 | 0.03343 | 0.0002336 |
| 15 | | | | 1.18 | 0.02440 | 0.03257 | 0.0004569 |
| 20 | | 2.65 | 0.00120 | 0.31 | 0.02201 | 0.01485 | 0.0006304 |
| 25 | | | | 0.09 | 0.01839 | 0.00391 | 0.0006161 |
| 30 | | 3.40 | 0.00080 | 0.02 | 0.01550 | 0.00107 | 0.0006163 |
| 40 | | 4.48 | 0.001157 | 0 | 0.01168 | 0.000202 | Div/0! |

TABLE 2

| Ca Results | | BOPPA | | pH ~3.0 ± 0.1 | | Dispersion Strip | 3M $H_2SO_4$ |
|---|---|---|---|---|---|---|---|
| Time (mins.) | pH | Strip (ppm) | Strip Flux g/(m²*hr) | Feed (ppm) | Ave. Flux g/(m²*hr) | Feed Flux g/(m²*hr) | k value cm/sec |
| 0 | 3.0 | 0 | | 87.2 | | | |
| 5 | | | | 32.2 | 0.943 | 0.943 | 0.000474 |
| 10 | | 578 | 0.619 | 5.3 | 0.702 | 0.462 | 0.000864 |

TABLE 2-continued

| Ca Results | BOPPA | | pH ~3.0 ± 0.1 | | Dispersion Strip | 3M H$_2$SO$_4$ |
|---|---|---|---|---|---|---|
| Time (mins.) | pH | Strip (ppm) | Strip Flux g/(m$^2$*hr) | Feed (ppm) | Ave. Flux g/(m$^2$*hr) | Feed Flux g/(m$^2$*hr) | k value cm/sec |
| 15 | | | | 0.00 | 0.498 | 0.090 | #DIV/0! |
| 20 | | 687 | 0.117 | 0.00 | 0.374 | 0.000 | #DIV/0! |
| 25 | | | | 0.00 | 0.299 | 0.0000 | #DIV/0! |
| 30 | | 701 | 0.0150 | 0.00 | 0.249 | 0.00000 | #DIV/0! |

TABLE 3

| Mg Results | BOPPA | | pH ~3.0 ± 0.1 | | Dispersion Strip | 3M H$_2$SO$_4$ |
|---|---|---|---|---|---|---|
| Time (mins.) | pH | Strip (ppm) | Strip Flux g/(m$^2$*hr) | Feed (ppm) | Ave. Flux g/(m$^2$*hr) | Feed Flux g/(m$^2$*hr) | k value cm/sec |
| 0 | 3.0 | 0 | | 23.1 | | | |
| 5 | | | | 22.1 | 0.0171 | 0.0171 | 0.0000211 |
| 10 | | 40.6 | 0.0431 | 18.2 | 0.0420 | 0.0669 | 0.0000925 |
| 15 | | | | 12.8 | 0.0589 | 0.0926 | 0.0001676 |
| 20 | | 82.7 | 0.0451 | 6.1 | 0.0730 | 0.115 | 0.0003553 |
| 25 | | | | 2.2 | 0.0715 | 0.0669 | 0.0004747 |
| 30 | | 140.00 | 0.06139 | 0.5 | 0.0645 | 0.0292 | 0.0006837 |

TABLE 4

| Zn Results | BOPPA | | pH ~3.0 ± 0.1 | | Dispersion Strip | 3M H$_2$SO$_4$ |
|---|---|---|---|---|---|---|
| Time (mins.) | pH | Strip (ppm) | Strip Flux g/(m$^2$*hr) | Feed (ppm) | Ave. Flux g/(m$^2$*hr) | Feed Flux g/(m$^2$*hr) | k value cm/sec |
| 0 | 3.0 | 0 | | 52.10 | | | |
| 5 | | | | 11.50 | 0.6960 | 0.6960 | 0.0007194 |
| 10 | | 332.0 | 0.03554 | 2.01 | 0.4293 | 0.1627 | 0.0008306 |
| 15 | | | | 0.45 | 0.2951 | 0.0267 | 0.0007127 |
| 20 | | 362.0 | 0.0321 | 0.10 | 0.2229 | 0.0060 | 0.0007362 |
| 25 | | | | 0.04 | 0.1785 | 0.0001 | 0.0004759 |
| 30 | | 379.0 | 0.01821 | 0.00 | 0.1489 | 0 | #DIV/0! |

Example 2

A fresh solution of 1 M HCl was prepared for use as the strip solution. A strip dispersion was then prepared by mixing together 250 ml of the 1 M HCl solution and 750 ml of n-dodecane containing 2% dodecanol and 8% BOPPA as described in the general procedure above. The strip dispersion was fed into the shell side of a polypropylene hollow fiber module. A feed solution containing the following metals was passed into the tube side of the hollow fiber module: strontium (Sr; 5 ppm), calcium (Ca; 80 ppm), magnesium (Mg; 20 ppm), or zinc (Zn; 50 ppm). The pH of the feed solution was maintained at 3.0+/−0.1 by adding 5 M NaOH as needed. Samples of the feed and strip solutions were collected at timed intervals as described in the general procedure above and analyzed by ICP. Fluxes and k values were then calculated and are reported in Tables 5 to 8. The 1 M HCl strip solution was found to be a better stripping agent than the than 3 M H$_2$SO$_4$.

TABLE 5

| Sr Results | BOPPA | | pH ~3.0 ± 0.1 | | Dispersion Strip | 1M HCl |
|---|---|---|---|---|---|---|
| Time (mins.) | pH | Strip (ppm) | Strip Flux g/(m$^2$*hr) | Feed (ppm) | Ave. Flux g/(m$^2$*hr) | Feed Flux g/(m$^2$*hr) | k value cm/sec |
| 0 | 3.0 | 0 | | 5.61 | | | |
| 5 | | | | 4.70 | 0.01560 | 0.01560 | 0.0000843 |
| 10 | | 1.04 | 0.000759 | 3.31 | 0.01971 | 0.02383 | 0.0001670 |
| 15 | | | | 1.98 | 0.02074 | 0.02280 | 0.0002447 |
| 20 | | 7.54 | 0.006864 | 1.04 | 0.01959 | 0.01611 | 0.0003066 |
| 25 | | | | 0.56 | 0.01731 | 0.00823 | 0.0002948 |

TABLE 5-continued

| Sr Results | | BOPPA | | pH ~3.0 ± 0.1 | | Dispersion Strip | 1M HCl |
|---|---|---|---|---|---|---|---|
| Time (mins.) | pH | Strip (ppm) | Strip Flux g/(m$^2$*hr) | Feed (ppm) | Ave. Flux g/(m$^2$*hr) | Feed Flux g/(m$^2$*hr) | k value cm/sec |
| 30 | | 12.6 | 0.00542 | 0.30 | 0.01518 | 0.00453 | 0.0003036 |
| 40 | | | | 0.77 | 0.011856 | 0.001877 | 0.000321 |
| 70 | | 17.6 | 0.001339 | 0 | 0.012021 | 0.00066 | #DIV/0! |

TABLE 6

| Ca Results | | BOPPA | | pH ~3.0 ± 0.1 | | Dispersion Strip | 1M HCl |
|---|---|---|---|---|---|---|---|
| Time (mins.) | pH | Strip (ppm) | Strip Flux g/(m$^2$*hr) | Feed (ppm) | Ave. Flux g/(m$^2$*hr) | Feed Flux g/(m$^2$*hr) | k value cm/sec |
| 0 | 3.0 | 0 | | 89.2 | | | |
| 5 | | | | 29.6 | 1.022 | 1.022 | 0.000525 |
| 10 | | 559 | 0.599 | 4.0 | 0.730 | 0.439 | 0.000955 |
| 15 | | | | 0.0 | 0.510 | 0.068 | #DIV/0! |
| 20 | | 653 | 0.101 | 0.0 | 0.382 | 0.000 | #DIV/0! |
| 25 | | | | 0.0 | 0.306 | 0.0000 | #DIV/0! |
| 30 | | 669 | 0.0171 | 0.0 | 0.255 | 0.00000 | #DIV/0! |

TABLE 7

| Mg Results | | BOPPA | | pH ~3.0 ± 0.1 | | Dispersion 1 M HCl Strip | |
|---|---|---|---|---|---|---|---|
| Time (mins.) | pH | Strip (ppm) | Strip Flux g/(m$^2$*hr) | Feed (ppm) | Ave. Flux g/(m$^2$*hr) | Feed Flux g/(m$^2$*hr) | k value cm/sec |
| 0 | 3.0 | | | 23.4 | | | |
| 5 | | | | 21.4 | 0.0343 | 0.0343 | 0.0000425 |
| 10 | | 40.6 | 0.0431 | 17.1 | 0.0540 | 0.0737 | 0.0001068 |
| 15 | | | | 12.7 | 0.0611 | 0.0754 | 0.0001417 |
| 20 | | 82.7 | 0.0451 | 8.6 | 0.0634 | 0.0702 | 0.0001856 |
| 25 | | | | 5.8 | 0.0603 | 0.0480 | 0.0001876 |
| 30 | | 140.0 | 0.06139 | 3.9 | 0.0558 | 0.0326 | 0.0001939 |
| 40 | | | | 1.5 | 0.046929 | 0.0412 | 0.000225 |
| 70 | | 144 | 0.001071 | 0.169 | 0.028446 | 0.0040 | 0.000173 |

TABLE 8

| Zn Results | | BOPPA | | pH ~3.0 ± 0.1 | | Dispersion 1 M HCl Strip | |
|---|---|---|---|---|---|---|---|
| Time (mins.) | pH | Strip (ppm) | Strip Flux g/(m$^2$*hr) | Feed (ppm) | Ave. Flux g/(m$^2$*hr) | Feed Flux g/(m$^2$*hr) | k value cm/sec |
| 0 | 3.0 | 0 | | 52.1 | | | |
| 5 | | | | 13.0 | 0.6703 | 0.6703 | 0.0006611 |
| 10 | | 318.0 | 0.3404 | 2.60 | 0.4243 | 0.1783 | 0.0007664 |
| 15 | | | | 0.78 | 0.2933 | 0.0313 | 0.0005764 |
| 20 | | 352.0 | 0.0364 | 0.28 | 0.2221 | 0.00860 | 0.0004848 |
| 25 | | | | 0.17 | 0.1780 | 0.00189 | 0.0002404 |
| 30 | | 364.0 | 0.01286 | 0.16 | 0.1484 | 0.00017 | 0.0000261 |
| 40 | | | | 0.126 | 0.111373 | 0.00059 | 5.69E−05 |
| 70 | | 385.0 | 0.005625 | 0 | 0.063796 | 0.00036 | #DIV/0! |

Example 3

A fresh solution of 3 M HCl was prepared for use as the strip solution. A strip dispersion was then prepared by mixing together 250 ml of the 3 M HCl solution and 750 ml of n-dodecane containing 2% dodecanol and 8% BOPPA as described in the general procedure above. The strip dispersion was fed into the shell side of a polypropylene hollow fiber module. A feed solution containing the following metals was passed into the tube side of the hollow fiber module: strontium (Sr; 5 ppm), calcium (Ca; 80 ppm), magnesium (Mg; 20 ppm), or zinc (Zn; 50 ppm). The pH of the feed solution was maintained at 3.0+/−0.1 by adding 5 M NaOH as needed. Samples of the feed and strip solutions were collected at timed intervals as described in the general procedure above and analyzed by ICP. Fluxes and k values were then calculated and are reported in Tables 9. No obvious improvement was seen using the 3 M HCL strip solution over the 1 M HCl strip solution.

TABLE 9

| Sr Results | BOPPA | | pH ~3.0 ± 0.1 | Dispersion | 3 M HCl Strip |
|---|---|---|---|---|---|
| Time (mins.) | pH | Strip (ppm) | Strip Flux g/(m$^2$*hr) | Feed (ppm) | Ave. Flux g/(m$^2$*hr) | Feed Flux g/(m$^2$*hr) | k value cm/sec |
| 0 | 3.0 | | | 5.49 | | | |
| 5 | | | | 5.01 | 0.00823 | 0.00823 | 0.0000436 |
| 10 | | 0.78 | 0.00048 | 3.19 | 0.01971 | 0.03120 | 0.0002150 |
| 15 | | | | 1.55 | 0.02251 | 0.02811 | 0.0003437 |
| 20 | | 6.61 | 0.006245 | 0.65 | 0.02075 | 0.01545 | 0.0004146 |
| 25 | | | | 0.24 | 0.01799 | 0.00696 | 0.0004678 |
| 30 | | 10.7 | 0.00438 | 0.08 | 0.01546 | 0.00279 | 0.0005291 |
| 40 | | | | 0.01 | 0.011743 | 0.0006 | 0.000495 |
| 70 | | 13.1 | 0.000643 | 0 | 0.011764 | 2.86E−05 | #DIV/0! |

TABLE 10

| Ca Results | BOPPA | | pH ~3.0 ± 0.1 | | Dispersion 3 M HCl Strip | |
|---|---|---|---|---|---|---|
| Time (mins.) | pH | Strip (ppm) | Strip Flux g/(m$^2$*hr) | Feed (ppm) | Ave. Flux g/(m$^2$*hr) | Feed Flux g/(m$^2$*hr) | k value cm/sec |
| 0 | 3.0 | 0 | | 88.6 | | | |
| 5 | | | | 31.4 | 0.981 | 0.981 | 0.000494 |
| 10 | | 558 | 0.598 | 3.74 | 0.727 | 0.474 | 0.001013 |
| 15 | | | | 0.00 | 0.506 | 0.064 | #DIV/0! |
| 20 | | 620 | 0.066 | 0.00 | 0.380 | 0.000 | #DIV/0! |
| 25 | | | | 0.00 | 0.304 | 0.0000 | #DIV/0! |
| 30 | | 620 | 0.0000 | 0.00 | 0.253 | 0.00000 | #DIV/0! |

TABLE 11

| Mg Results | BOPPA | | pH ~3.0 ± 0.1 | | Dispersion 3 M HCl Strip | |
|---|---|---|---|---|---|---|
| Time (mins.) | pH | Strip (ppm) | Strip Flux g/(m$^2$*hr) | Feed (ppm) | Ave. Flux g/(m$^2$*hr) | Feed Flux g/(m$^2$*hr) | k value cm/sec |
| 0 | 3.0 | 0 | | 25.3 | | | |
| 5 | | | | 24.5 | 0.0137 | 0.0137 | 0.0000153 |
| 10 | | 22.6 | 0.0239 | 20.5 | 0.0411 | 0.0686 | 0.0000849 |
| 15 | | | | 13.2 | 0.0691 | 0.1251 | 0.0002096 |
| 20 | | 61.0 | 0.0411 | 7.60 | 0.0759 | 0.09597 | 0.0002629 |
| 25 | | | | 4.33 | 0.0719 | 0.0560 | 0.0002679 |
| 30 | | 90.2 | 0.03129 | 2.04 | 0.0665 | 0.0394 | 0.0003584 |
| 40 | | | | 0.65 | 0.052821 | 0.0240 | 0.000272 |
| 70 | | 115.0 | 0.006643 | 0.22 | 0.03071 | 0.00123 | 8.6E−05 |

TABLE 12

| Zn Results | BOPPA | | pH ~3.0 ± 0.1 | | Dispersion 1 M HCl Strip | |
|---|---|---|---|---|---|---|
| Time (mins.) | pH | Strip (ppm) | Strip Flux g/(m$^2$*hr) | Feed (ppm) | Ave. Flux g/(m$^2$*hr) | Feed Flux g/(m$^2$*hr) | k value cm/sec |
| 0 | 3.0 | 0 | | 51.8 | | | |
| 5 | | | | 10.1 | 0.7149 | 0.7149 | 0.0007785 |
| 10 | | 298 | 0.3189 | 1.47 | 0.4314 | 0.1479 | 0.0009177 |
| 15 | | | | 0.27 | 0.2944 | 0.0205 | 0.0008017 |
| 20 | | 321 | 0.0246 | 0.21 | 0.2211 | 0.00102 | 0.0001249 |

TABLE 12-continued

| Zn Results | | BOPPA | | pH ~3.0 ± 0.1 | | Dispersion 1 M HCl Strip | |
|---|---|---|---|---|---|---|---|
| Time (mins.) | pH | Strip (ppm) | Strip Flux g/(m²*hr) | Feed (ppm) | Ave. Flux g/(m²*hr) | Feed Flux g/(m²*hr) | k value cm/sec |
| 25 | | | | 0.08 | 0.1773 | 0.00222 | 0.0004596 |
| 30 | | 328 | 0.00750 | 0.23 | 0.1473 | −0.00256 | ######## |
| 40 | | | | 0.07 | 0.11085 | 0.00273 | 0.000287 |
| 70 | | 328 | 0 | 0 | 0.063429 | 0.00020 | #DIV/0! |

Example 4

A fresh solution of 1 M HCl was prepared for use as the strip solution. A strip dispersion was then prepared by mixing together 250 ml of the 1 M HCl solution and 750 ml of n-dodecane containing 2% dodecanol and 8% BOPPA as described in the general procedure above. The strip dispersion was fed into the shell side of a polypropylene hollow fiber module. A feed solution containing the following metals was passed into the tube side of the hollow fiber module: strontium (Sr; 5 ppm), calcium (Ca; 80 ppm), magnesium (Mg,; 20 ppm), or zinc (Zn; 50 ppm). The pH of the feed solution was maintained at 2.5+/−1.0 by adding 5 M NaOH as needed. Samples of the feed and strip solutions were collected at timed intervals as described in the general procedure above and analyzed by ICP. Fluxes and k values were then calculated and are reported in Tables 13 to 16. The results of the extraction at pH 2.5 was slightly worse than those at pH 3, but most of the Sr was removed after 70 minutes.

TABLES 13

| Sr Results | | BOPPA | | pH ~2.5 ± 0.1 | | Dispersion 1 M HCl Strip | |
|---|---|---|---|---|---|---|---|
| Time (mins.) | pH | Strip (ppm) | Strip Flux g/(m²*hr) | Feed (ppm) | Ave. Flux g/(m²*hr) | Feed Flux g/(m²*hr) | k value cm/sec |
| 0 | 2.5 | 0 | | 5.42 | | | |
| 5 | | | | 5.19 | 0.00394 | 0.00394 | 0.0000206 |
| 10 | | 4.13 | 0.00407 | 4.74 | 0.00583 | 0.00771 | 0.0000432 |
| 15 | | | | 3.75 | 0.00954 | 0.01697 | 0.0001116 |
| 20 | | 5.52 | 0.001489 | 3.05 | 0.01016 | 0.01200 | 0.0000984 |
| 25 | | | | 2.39 | 0.01039 | 0.01131 | 0.0001161 |
| 30 | | 7.43 | 0.00205 | 1.85 | 0.01020 | 0.00926 | 0.0001220 |
| 40 | | | | 1.13 | 0.009193 | 0.006171 | 0.000117 |
| 70 | | 12.3 | 0.001304 | 0.322 | 0.010924 | 0.002309 | 0.000299 |

TABLES 14

| Ca Results | | BOPPA | | pH ~2.5 ± 0.1 | | Dispersion 1 M HCl Strip | |
|---|---|---|---|---|---|---|---|
| Time (mins.) | pH | Strip (ppm) | Strip Flux g/(m²*hr) | Feed (ppm) | Ave. Flux g/(m²*hr) | Feed Flux g/(m²*hr) | k value cm/sec |
| 0 | 2.5 | 0 | | 87.2 | | | |
| 5 | | | | 40.3 | 0.804 | 0.804 | 0.000368 |
| 10 | | 281 | 0.301 | 8.66 | 0.673 | 0.542 | 0.000732 |
| 15 | | | | 0.00 | 0.498 | 0.148 | #DIV/0! |
| 20 | | 350 | 0.074 | 0.00 | 0.374 | 0.000 | #DIV/0! |
| 25 | | | | 0.00 | 0.299 | 0.0000 | #DIV/0! |
| 30 | | 353 | 0.0032 | 0.00 | 0.249 | 0.00000 | #DIV/0! |

TABLE 15

| Mg Results | | BOPPA | | pH ~2.5 ± 0.1 | | Dispersion 1 M HCl Strip | |
|---|---|---|---|---|---|---|---|
| Time (mins.) | pH | Strip (ppm) | Strip Flux g/(m²*hr) | Feed (ppm) | Ave. Flux g/(m²*hr) | Feed Flux g/(m²*hr) | k value cm/sec |
| 0 | 2.5 | 0 | | 26.8 | | | |
| 5 | | | | 26.5 | 0.0051 | 0.0051 | 0.0000054 |
| 10 | | 22.6 | 0.0239 | 25.3 | 0.0129 | 0.0206 | 0.0000221 |

TABLE 15-continued

| Mg Results | BOPPA | | pH ~2.5 ± 0.1 | | Dispersion 1 M HCl Strip | |
|---|---|---|---|---|---|---|
| Time (mins.) | pH | Strip (ppm) | Strip Flux g/(m²*hr) | Feed (ppm) | Ave. Flux g/(m²*hr) | Feed Flux g/(m²*hr) | k value cm/sec |
| 15 | | | | 22.7 | 0.0234 | 0.0446 | 0.0000516 |
| 20 | | 61.0 | 0.0411 | 20.5 | 0.0270 | 0.0377 | 0.0000485 |
| 25 | | | | 18.4 | 0.0288 | 0.0360 | 0.0000515 |
| 30 | | 90.2 | 0.03129 | 16.0 | 0.0309 | 0.0411 | 0.0000666 |
| 40 | | | | 12.2 | 0.031286 | 0.0651 | 6.46E−05 |
| 70 | | 115 | 0.006643 | 5.66 | 0.025886 | 0.00211 | 6.1E−05 |

TABLE 16

| Zn Results | BOPPA | | pH ~2.5 ± 0.1 | | Dispersion 1 M HCl Strip | |
|---|---|---|---|---|---|---|
| Time (mins.) | pH | Strip (ppm) | Strip Flux g/(m²*hr) | Feed (ppm) | Ave. Flux g/(m²*hr) | Feed Flux g/(m²*hr) | k value cm/sec |
| 0 | 2.5 | 0 | | 53.8 | | | |
| 5 | | | | 13.2 | 0.6960 | 0.6960 | 0.0006691 |
| 10 | | 187 | 0.2000 | 2.36 | 0.4409 | 0.1858 | 0.0008198 |
| 15 | | | | 0.30 | 0.3057 | 0.0352 | 0.0009759 |
| 20 | | 203 | 0.0171 | 0.00 | 0.2306 | 0.00513 | #DIV/0! |
| 25 | | | | 0.00 | 0.1845 | 0 | #DIV/0! |
| 30 | | 206 | 0.00321 | 0.00 | 0.1537 | 0 | #DIV/0! |
| 40 | | | | 0.00 | 0.115286 | 0 | #DIV/0! |
| 70 | | 208 | 0.000536 | 0 | 0.065878 | 0 | #DIV/0! |

Example 5

Comparison Between BOPPA and DEHPA

The experimental procedure for this example using di(2-yl-1-hexyl) phosphoric acid (DEHPA) with feed pH 2.5 was similar to that described in Example 4 except DEHPA was used instead of BOPPA. Fluxes and k values for strontium were calculated and are reported in Table 17. As shown in Table 17, and as compared with the results in Example 4, the strontium removal results with DEHPA at feed pH 2.5 were poor and much worse than those with BOPPA. In addition, an experiment using DEHPA at feed pH 4.5 resulted in the formation of white solid precipitates in the feed solution, presumably from the formation of a solid complex between DEHPA and zinc in the feed solution. The precipitates blocked the flow of the feed through the module and stopped the experiment. Therefore, the BOPPA extractant is much better than the DEHPA extractant for the removal of strontium.

TABLE 17

| Sr Results | BOPPA | | pH ~2.5 ± 0.1 | | Dispersion 1 M HCl Strip | |
|---|---|---|---|---|---|---|
| Time (mins.) | pH | Strip (ppm) | Strip Flux g/(m²*hr) | Feed (ppm) | Ave. Flux g/(m²*hr) | Feed Flux g/(m²*hr) | k value cm/sec |
| 0 | 2.5 | 0 | | 5.42 | | | |
| 5 | | | | 5.20 | 0.00377 | 0.00377 | 0.0000197 |
| 10 | | 9.11 | 0.007520 | 5.03 | 0.00334 | 0.00291 | 0.0000158 |
| 15 | | | | 4.86 | 0.00320 | 0.00291 | 0.0000164 |
| 20 | | 9.73 | 0.000531 | 4.49 | 0.00399 | 0.00634 | 0.0000377 |
| 25 | | | | 4.21 | 0.00415 | 0.00480 | 0.0000307 |
| 30 | | 11.9 | 0.001860 | 3.96 | 0.00417 | 0.00429 | 0.0000292 |

Example 6

The experimental procedure for this example was the same as that described in Example 2, except that 2-hexyl-1-decyl phenylphosphonic acid (C16 HDPPA) was used instead of BOPPA. Fluxes and k values for strontium were calculated and are reported in Table 18. As shown in this table, the C16 HDPPA extractant removed strontium very well.

TABLE 18

| Sr Results | C16 HDPPA | | pH ~3.0 ± 0.1 | | Dispersion 1 M HCl Strip | |
| --- | --- | --- | --- | --- | --- | --- |
| Time (mins.) | pH | Strip (ppm) | Strip Flux g/(m²*hr) | Feed (ppm) | Ave. Flux g/(m²*hr) | Feed Flux g/(m²*hr) | k value cm/sec |
| 0 | 3.0 | 0 | | 5.53 | | | |
| 10 | | 3.12 | 0.00334 | 4.58 | 0.00814 | 0.00814 | 0.0000449 |
| 20 | | 20.30 | 0.01841 | 1.79 | 0.01603 | 0.02391 | 0.0002237 |
| 40 | | 39.00 | 0.00889 | 0.00 | 0.01185 | 0.00767 | #DIV/0! |

Example 7

Comparison Between C16 HDPPA and C16 DEHPA

The experimental procedure for this example using di(2-hexyl-1-decyl)phosphoric acid (C16 DEHPA) was the same as that described in Examples 2 and 6, except that C16 DEHPA was used instead of BOPPA or C16 HDPPA. Fluxes and k values for strontium were calculated and are reported in Table 19. As shown in this table and as compared with the results in Example 6, the strontium removal results with C16 DEHPA were poor and much worse than those with C16 HDPPA. In addition, the strip dispersion with C16 DEHPA turned into an emulsion, and it was difficult to separate into two phases, the organic liquid phase and the aqueous strip phase, upon standing. In other words, the C16 HDPPA extractant was much better than the C16 DEHPA extractant for the removal of strontium.

TABLE 19

| Sr Results | C16 DEHPA | | pH ~3.0 ± 0.1 | | Dispersion 1 M HCl Strip | |
| --- | --- | --- | --- | --- | --- | --- |
| Time (mins.) | pH | Strip (ppm) | Strip Flux g/(m²*hr) | Feed (ppm) | Ave. Flux g/(m²*hr) | Feed Flux g/(m²*hr) | k value cm/sec |
| 0 | 3.0 | 0 | | 5.53 | | | |
| 10 | | | | 5.04 | 0.00420 | 0.00420 | 0.0000221 |
| 20 | | | | 4.67 | 0.00369 | 0.00317 | 0.0000182 |
| 30 | | | | 3.44 | 0.00597 | 0.01054 | 0.0000728 |
| 40 | | 8.27 | 0.00443 | 1.73 | 0.00814 | 0.01466 | 0.0001637 |

Example 8

The experimental procedure for this example was the same as that described in Example 2, except that a mixture of 2-hexyl-1-dodecyl/2-octyl-1-decyl phenylphosphonic acids (C18 HDPPA/ODPPA) was used instead of BOPPA. Fluxes and k values for strontium were calculated and are reported in Table 20. As shown in this table, the C18 HDPPA/ODPPA extractant mixture removed strontium very well.

TABLE 20

| Sr Results | | C18 HDPPA/ ODPPA | | pH ~3.0 +/− 0.1 | | Dispersion 1 M HCl Strip | |
|---|---|---|---|---|---|---|---|
| Time (mins.) | pH | Strip (ppm) | Strip Flux g/(m² * hr) | Feed (ppm) | Ave. Flux g/(m² * hr) | Feed Flux g/(m² * hr) | k value cm/sec |
| 0 | 3.0 | 0 | | 6.26 | | | |
| 10 | | 3.39 | 0.00363 | 5.73 | 0.00454 | 0.00454 | 0.0000211 |
| 20 | | 26.7 | 0.02498 | 1.81 | 0.01907 | 0.03360 | 0.0002744 |
| 30 | | | | 0.015 | 0.01784 | 0.01539 | 0.0011412 |
| 40 | | 49.7 | 0.01232 | 0.00 | 0.01341 | 0.00013 | #DIV/0! |

Example 9

The experimental procedure for this example was the same as that described in Example 2, except that 2-octyl-1-dodecyl phenylphosphonic acid (C20 ODPPA) was used instead of BOPPA. Fluxes and k values for strontium were calculated and are reported in Table 21. As shown in this table, the C20 ODPPA extractant removed strontium very well.

TABLE 21

| Sr Results | | C20 ODPPA | | pH ~3.0 +/− 0.1 | | Dispersion 1 M HCl Strip | |
|---|---|---|---|---|---|---|---|
| Time (mins.) | pH | Strip (ppm) | Strip Flux g/(m² * hr) | Feed (ppm) | Ave. Flux g/(m² * hr) | Feed Flux g/(m² * hr) | k value cm/sec |
| 0 | 3.0 | 0 | | 5.30 | | | |
| 10 | | | | 4.88 | 0.00360 | 0.00360 | 0.0000197 |
| 20 | | | | 3.06 | 0.00960 | 0.01560 | 0.0001111 |
| 30 | | | | 0.32 | 0.01423 | 0.02349 | 0.0005376 |
| 40 | | 28.00 | 0.00750 | 0.00 | 0.01136 | 0.00274 | #DIV/0! |

Example 10

Radioactive Strontium-90 Experiments

A series of ten experiments using the combined supported liquid membrane (SLM)/strip dispersion process of the present invention were carried out by the use of radioactive strontium-90. For these experiments, the experimental procedure and conditions were similar to those described earlier in the general procedure except those noted below specifically. The following paragraphs describe the EXPERIMENTS, RESULTS, and CONCLUSIONS.

Experiments

Two separate organic solutions were used in the experiments. The first organic solution was freshly prepared with a composition of 8 wt % C20 ODPPA, 2 wt % dodecanol, and 90 wt % dodecane (42.6 g of C20 ODPPA), which was used in Experiments #1, 2, 3, and 4 with a low feed concentration of 317 pico Curie per liter (pCi/L) strontium-90 and Experiment #9 with a low feed concentration of 1,000 pCi/L. This solution was also used later in Experiment #10 with a high feed concentration of 487,000 pCi/L Sr-90. The second organic solution used for Experiments #5 and 6 with a low feed concentration of 1,000 pC/L Sr-90 and for Experiments #7 and 8 with a high feed concentration of 27,941 pCi/L was made from two used solutions of the same composition employed in Experiments #1, 2, 3, 4, and 9 with the low feed concentrations.

The strip dispersions were made up of 1.0 M HCl and the previously mentioned organic solutions. The total strip dispersion volume used was about 1 L (0.25 L acid strip solution and 0.75 L organic solution), except for Experiments #7, 8, and 10 where 0.6 L was used (#7 and 8 with 0.1 L acid strip solution and 0.5 L organic solution, #10 with 0.040 L acid solution and 0.560 L organic solution). A fresh acid strip solution was used for each experiment.

All of the feed solutions were run at a pH of 3.0. The pH was maintained between 2.9 and 3.0 by the addition of 5.0 M NaOH. Four different feed solutions were used. As mentioned, Experiments #1–4 used a feed solution of 317 pCi/L. Experiments #5, 6, and 9 used a feed solution of 1,000 pCi/L. Experiments #7 and 8 used a feed solution of about 27,941 pCi/L. Experiment #10 used a feed solution of about 487,000 pCi/L. All of the runs except Experiment #10 used two liters of feed solution. Experiment #10 used one liter of feed. All of the runs used ground water. The aqueous feed solutions for Experiments #4, 6, 8, and 9 had calcium, magnesium, and zinc added to them to make their concentrations of about 80 ppm, 20 ppm, and 50 ppm, respectively.

For these experiments, the feed outlet pressure was maintained between 4–4.5 psi, and the strip dispersion inlet pressure was maintained between 1–2 psi. The feed inlet pressure was maintained between 5–5.5 psi.

Samples were taken during the experiments from the discharge of the module and not from the bulk solution. The sample volumes taken were at least 100 mL. Two strip samples were analyzed after diluting the sample 1:100. The strontium-90 concentrations were measured by filtering the sample through 3M's EMPORE® filter paper, which selectively traps about 97% of Sr-90. The samples were prepared in the following manner per the manufacturer's directions. Concentrated nitric acid was added to the sample to make a 2.0 N nitric acid solution. The sample was then stirred and allowed to sit. One of the filter papers was placed in a filter support and conditioned with 10 mL of methanol for approximately 1 minute. After one minute, the methanol was pulled through the filter, followed immediately by 20 mL of 2.0 M $HNO_3$. Immediately following the nitric acid, the sample was added to the filter. The directions called for the sample to be passed through the filter at a rate of about 50 mL/min. Most of the samples were passed through the filter at no more than 25 mL/min; this ensured the capture of Sr-90 by the filter. The sample was immediately followed by 20 mL of 2.0 M $HNO_3$. The filter was then dried under a heat lamp and was analyzed by a gas flow proportional counter, Tennelec 1000 series, Low Background Alpha/Beta Counting System. Due to a limited number of filters and the expense of each filter, only selected samples were analyzed.

Results

Low Feed Concentration Experiments

Experiments #1, 2, and 3 were all done using the same parameters and 317 pCi/L Sr-90 starting concentration. In all of these experiments, the target concentration of below 8 pCi/L in the treated ground water was achieved. In Experiment #4 with calcium, magnesium, and zinc added to the feed water, the Sr-90 was reduced to below the target concentration within four hours. The data from these experiments along with all of the rest of the ten experiments are shown in Table 22 at the end of this example. Also included in this table are the mass transfer coefficient k values determined from all of the experiments.

Three experiments using the C20 ODPPA extractant were done using a starting Sr-90 concentration of 1,000 pCi/L. One run was made with just Sr-90, and a second run was made using Sr-90 with calcium, magnesium, and zinc, Experiments #5 and 6, respectively. The third experiment, Experiment #9, was done with the feed containing Sr-90, calcium, magnesium, and zinc. In all three of these experiments, the treated feed concentration was expected to reach about 50 pCi/L Sr-90. All these experiments reached or exceeded that goal. Experiments #9 reduced the Sr-90 concentration in the feed to <8 pCi/L.

High Concentration Experiments

Two experiments, #7 and 8, were done using a starting feed concentration of about 27,941 pCi/L Sr-90. Both experiments were done using a reduced strip and organic volumes of 0.100 L and 0.500 L, respectively. In Experiment #7, the final Sr-90 concentration in the feed after three hours was 222 pCi/L. The strip Sr-90 concentration was tested after three hours and was found to be about 60,000 pCi/L. The concentration was expected to be much higher, about 300,000 pCi/L. The lack of concentration in the strip was probably due to a significant amount of the strip solution trapped in the module from the previous run. This effectively increased the volume of the strip solution, reducing the maximum concentration of Sr-90 achievable in the strip solution. This trapped liquid was not purged (which could be done with air purging, if available), and it was present in all of the experiments. Experiment #8 added calcium, magnesium, and zinc to the feed in addition to 27,941 pCi/L of Sr-90. At the end of five hours, the Sr-90 concentration in the feed was 84.0 pCi/L, and the strip concentration was 263,382 pCi/L. The feed result was better than expected, and the strip result was acceptable.

One other experiment was run, Experiment #10 using the used organic solution from Experiments #1, 2, 3, and 4. The strip solution volume was reduced to 0.040 L, and 0.560 L of the organic solution was used. The experiment was run for three hours, and it had a final feed Sr-90 concentration of 1,562 pCi/L, reduced from about the initial concentration of 487,000 pCi/L, and a final strip concentration of 1,219,577 pCi/L.

CONCLUSIONS

It has been demonstrated that Sr-90 can be removed from ground water solutions effectively with the combined supported liquid membrane/strip dispersion process of the present invention. This process was very effective to remove Sr-90 from feed solutions containing about 300–1,000 pCi/L Sr-90 to the target concentration of less than 8 pCi/L in the treated feed solutions. Especially, this target concentration was also achieved from a ground water solution containing about 1,000 pCi/L Sr-90, 80 ppm calcium, 20 ppm magnesium, and 50 ppm zinc. The feed solutions used containing these ions simulated the ground waters at Brookhaven National Laboratory and West Valley, N.Y.

Two strip solutions were generated with Sr-90 concentrations above 250,000 pCi/L. The first was generated from a feed solution of 27,941 pCi/L and resulted in a Sr-90 strip concentration of 263,382 pCi/L. The second was generated from a feed solution of about 497,000 pCi/L and resulted in a Sr-90 strip concentration of 1,216,577 pCi/L.

The new extractant, C20 ODPPA, was very effective for the removal of Sr-90, and it gave consistent results below 8 pCi/L Sr-90 in the treated feed solutions. The treated feed and used strip solution samples that were analyzed did not have any problems while filtering and did not have any cloudiness, indicating insignificant solubility of this extractant in the aqueous feed and strip solutions.

TABLE 22

Strontium-90 Testing Results

| Run | Sample | Time min | Sample size g | Sr-90 conc.* pCi/L | $k^{++}$ Sr-90 cm/s |
|---|---|---|---|---|---|
| 1 | Feed | 120 | 257.6 | 3.30 | 7.94E-05 |
| 2 | Feed | 120 | 261.2 | 3.46 | 7.83E-05 |
| 3 | Feed | 120 | 257.4 | 3.34 | 9.03E-05 |
| 3 | Feed | 180 | 251.5 | 4.41 | — |
| 4 | Feed | 0 | 128.2 | 317 | — |
| 4 | Feed | 240 | 260.2 | 4.00 | 3.78E-05 |
| 5 | Feed | 60 | 124.2 | 99.4 | 1.08E-04 |
|   |   |   |   | 32.7 |   |
|   |   |   |   | Avg.66.0** |   |
| 5 | Feed | 120 | 125.6 | 110 | — |
|   |   |   |   | 64.6 |   |
|   |   |   |   | 146 |   |
|   |   |   |   | Avg. 107** |   |
| 6 | Feed | 240 | 247.3 | 5.52 | 4.83E-05 |
| 7 | Feed | 0 | 127.9 | 27,941 | — |
| 7 | Feed | 60 | 119.5 | 1,171 | 1.18E-04 |
| 7 | Feed | 120 | 125.3 | 352 | 4.18E-05 |
| 7 | Feed | 180 | 121.3 | 222 | 1.48E-05 |
| 8 | Feed | 300 | 129.7 | 84.0 | 4.61E-05 |
| 8 | Strip | 300 | 135.2 | 263,382 | — |
| 9 | Feed | 360 | 1024.5 | 0.979 | 4.58E-05 |
| 10 | Feed | 180 | 120.6 | 1,562 | 3.81E-05 |
| 10 | Strip | 180 | 1 | 1,219,577 | — |

*Strontium 90 concentration corrected for 97% removal efficiency of the filters and Y-90 in-growth as a function of time from the preparation of the filtered sample to the radioactivity counting analysis.
**Average of the shown analyses
++Mass transfer coefficients were calculated using 317 pCi/L, 1,000 pCi/L, 27,941 pCi/L and 487,000 pCi/L feed concentrations for the respective experiments.

Example 11

2-Butyl-1-octyl (C12) phenylphosphonic acid (BOPPA) was synthesized by the following reaction. A solution of 45 g of 2-butyl-1-octanol in 100 ml of pyridine was prepared. A solution of 51 g of phenylphosphonyl dichloride in 100 ml of pyridine was also prepared. The 2-butyl-1-octanol solution was added dropwise to the phenyl phosphonyl dichloride solution at a temperature between 5 and 10° C. over a period of 30 minutes. The reaction was then allowed to continue at the same temperature for an additional hour while the mixture was stirred. Then, 300 ml of concentrated HCl and about 200 g of ice were added to the reaction mixture, resulting in a solution having a pH of 1. The BOPPA was then extracted from the reaction mixture with 200 ml of toluene. The BOPPA/toluene solution was washed with 200 ml of 1 M HCl solution and dried with $MgSO_4$ to produce a clear solution. BOPPA (60 g) was obtained by evaporating the toluene at 60° C. for 30 minutes.

Example 12

BOPPA was also synthesized by the following reaction (with different reactant amounts from those used in Example 11). A solution of 31.5 g of 2-butyl-1-octanol in 70 ml of pyridine was prepared. A solution of 44 g of phenylphosphonyl dichloride in 70 ml of pyridine was also prepared. The 2-butyl-1-octanol solution was added dropwise to the phenyl phosphonyl dichloride solution at a temperature between 5 and 10° C. over a period of 30 minutes. The reaction was then allowed to continue at the same temperature for an additional 4–8 hours while the mixture was stirred. Then, 200 ml of concentrated HCl and about 200 g of ice were added to the reaction mixture, resulting in a solution having a pH of approximately 1. The mixture was allowed to stir for 24 hours. The BOPPA was then extracted from the reaction mixture with 200 ml of toluene. The BOPPA/toluene solution was washed with 200 ml of 1 M HCl solution and dried with $MgSO_4$ to produce a clear solution. BOPPA at a yield of about 90% based on the alcohol reactant was obtained by evaporating the toluene at 80° C. for approximately 30 minutes.

Example 13

2-Hexyl-1-decyl phenylphosphonic acid (C16 HDPPA) was synthesized by the use of the same procedure described in Example 12 except 41 g of 2-hexyl-1-decanol was used instead of 31.5 g, of 2-butyl-1-octanol.

Example 14

2-Octyl-1-decyl/2-hexyl-1-dodecyl phenylphosphonic acid (C18 ODPPA/HDPPA) was synthesized by the use of the same procedure described in Example 12 except 45.7 g of a mixture of 2-octyl-1-decanol and 2-hexyl-1-dodecanol was used instead of 31.5 g of 2-butyl-1-octanol.

Example 15

2-Octyl-1-dodecyl phenylphosphonic acid (C20 ODPPA) was synthesized by the use of the same procedure described in Example 12 except 50.5 g of 2-octyl-1-dodecanol was used instead of 31.5 g, of 2-butyl-1-octanol.

What is claimed is:

1. A combined supported liquid membrane (SLM)/strip dispersion process for the removal and recovery of one or more radionuclides or one or more metals from a feed solution containing the radionuclides comprising
    (1) treating a feed solution containing one or more radionuclides or one or more metals by passing the feed solution on one side of the SLM embedded in a microporous support material and removing the radionuclides by the use of a strip dispersion on the other side of the SLM, the strip dispersion being formed by dispersing an aqueous strip solution in an organic liquid comprising an extractant using a mixer; and
    (2) allowing the strip dispersion or a part of the strip dispersion to separate into two phases, the organic liquid phase and the aqueous strip solution phase containing a concentrated radionuclide or metal solution.

2. The process of claim 1 wherein the radionuclide is selected from the group consisting of strontium, cesium, technetium, uranium, boron, plutonium, cobalt, americium, and mixtures thereof.

3. The process of claim 1 wherein the feed solution is treated to remove strontium to a concentration of 8 pico Curie per liter (8 pCi/L) or lower.

4. The process of claim 1 wherein the metal is selected from the group consisting of calcium, magnesium, zinc, and mixtures thereof.

5. The process of claim 1 wherein the aqueous strip solution of the strip dispersion comprises an acid.

6. The process of claim 5 wherein the acid is selected from the group consisting of sulfuric acid, hydrochloric acid, nitric acid, acetic acid, and mixtures thereof.

7. The process of claim 1 wherein the organic liquid of the strip dispersion further comprises a modifier in a hydrocarbon solvent or mixtures thereof.

8. The process of claim 1 wherein the organic liquid of the strip dispersion comprises about 2 wt. % to about 100 wt. % extractant and about 0 wt. % to about 20 wt. % modifier in a hydrocarbon solvent or mixtures thereof.

9. The process of claim 8 wherein the organic liquid of the strip dispersion comprises about 5 wt. % to about 40 wt. % extractant and about 1 wt. % to about 10 wt. % modifier in a hydrocarbon solvent or mixtures thereof.

10. The process of claim 7 wherein the modifier is selected from the group consisting of alcohols, nitrophenyl alkyl ethers, trialkyl phosphates, and mixtures thereof.

11. The process of claim 10 wherein the alcohol is selected from the group consisting of hexanol, heptanol, octanol, nonanol, decanol, undecanol, dodecanol, tridecanol, tetradecanol, pentadecanol, hexadecanol, heptadacanol, octadecanol, and mixtures thereof.

12. The process of claim 10 wherein the nitrophenyl alkyl ether is selected from the group consisting of o-nitrophenyl octyl ether (o-NPOE), o-nitrophenyl heptyl ether, o-nitrophenyl hexyl ether, o-nitrophenyl pentyl ether (o-NPPE), o-nitrophenyl butyl ether, o-nitrophenyl propyl ether, and mixtures thereof.

13. The process of claim 10 wherein the trialkyl phosphate is selected from the group consisting of tributyl phosphate, tris(2-ethylhexyl)phosphate, and mixtures thereof.

14. The process of claim 7 wherein the hydrocarbon solvent is selected from a group consisting of n-decane; n-undecane; n-dodecane; n-tridecane; n-tetradecane; isodecane; isoundecane; isododecane; isotridecane; isotetradecane; isoparaffinic hydrocarbon solvent having a flash point of 92° C., a boiling point of 254° C., a viscosity of 3 cp at 25° C., and a density of 0.791 g/ml at 15.6° C.; and mixtures thereof.

15. The process of claim 1 wherein the microporous support material is selected from the group consisting of polypropylene, polytetrafluoroethylene, polyethylene, polysulfone, polyethersulfone, polyetheretherketone, polyimide, polyamide, and mixtures thereof.

16. The process of claim 1 wherein the extractant comprises an alkyl phenylphosphonic acid.

17. The process of claim 16 wherein the alkyl group of the alkyl phenylphosphonic acid is paraffinic (saturated) and has from 6 to 26 carbon atoms.

18. The process of claim 16 wherein the alkyl phenylphosphonic acid is selected from the group consisting of 2-butyl-1-octyl phenylphosphonic acid (BOPPA), 2-hexyl-1-decyl phenylphosphonic acid, 2-octyl-1-decyl/2-hexyl-1-dodecyl phenylphosphonic acid, 2-octyl-1-dodecyl phenylphosphonic acid, hexyl phenylphosphonic acid, heptyl phenylphosphonic acid, octyl phenylphosphonic acid, nonyl phenylphosphonic acid, decyl phenylphosphonic acid, undecyl phenylphosphonic acid, dodecyl phenylphosphonic acid, tridecyl phenylphosphonic acid, tetradecyl phenylphosphonic acid, pentadecyl phenylphosphonic acid, hexadecyl phenylphosphonic acid, heptadecyl phenylphosphonic acid, octadecyl phenylphosphonic acid, nonadecyl phenylphosphonic acid, decadecyl phenylphosphonic acid, undecadecyl phenylphosphonic acid, dodecadecyl phenylphosphonic acid, tridecadecyl phenylphosphonic acid, tetrdecadecyl phenylphosphonic acid, pentadadecyl phenylphosphonic acid, hexadecadecyl phenylphosphonic acid, and mixtures thereof.

19. The process of claim 16 wherein the alkyl phenylphosphonic acid is 2-butyl-1-octyl phenylphosphonic acid (BOPPA).

20. The process of claim 16 wherein the alkyl phenylphosphonic acid is 2-hexyl-1-decyl phenylphosphonic acid.

21. The process of claim 16 wherein the alkyl phenylphosphonic acid is 2-octyl-1-decyl/2-hexyl-1-dodecyl phenylphosphonic acid.

22. The process of claim 16 wherein the alkyl phenylphosphonic acid is 2-octyl-1-dodecyl phenylphosphonic acid.

23. The process of claim 16 for the removal of one or more radionuclides.

24. The process of claim 23 wherein the radionuclide is selected from the group consisting of strontium, cesium, plutonium, cobalt, americium, and mixtures thereof.

25. The process of claim 24 for the removal of strontium.

26. The process of claim 25 wherein alkyl phenylphosphonic acid is 2-butyl-1-octyl phenylphosphonic acid (BOPPA).

27. The process of claim 25 wherein the alkyl phenylphosphonic acid is 2-hexyl-1-decyl phenylphosphonic acid.

28. The process of claim 25 wherein the alkyl phenylphosphonic acid is 2-octyl-1-decyl/2-hexyl-1-dodecyl phenylphosphonic acid.

29. The process of claim 25 wherein the alkyl phenylphosphonic acid is 2-octyl-1-dodecyl phenylphosphonic acid.

30. The process of claim 16 for the removal of metal.

31. The process of claim 30 wherein the metal is selected from the group consisting of calcium, magnesium, zinc, and mixtures thereof.

32. The process of claim 31 wherein the alkyl phenylphosphonic acid is 2-butyl-1-octyl phenylphosphonic acid.

33. The process of claim 31 wherein the alkyl phenylphosphonic acid is 2-hexyl-1-decyl phenylphosphonic acid.

34. The process of claim 31 wherein the alkyl phenylphosphonic acid is 2-octyl-1-decyl/2-hexyl-1-dodecyl phenylphosphonic acid.

35. The process of claim 31 wherein the alkyl phenylphosphonic acid is 2-octyl-1-dodecyl phenylphosphonic acid.

* * * * *